United States Patent [19]

Marciniak et al.

[11] Patent Number: 5,175,188
[45] Date of Patent: Dec. 29, 1992

[54] ASCORBIC ACID DERIVATIVES

[75] Inventors: Gilbert Marciniak, Strasbourg; J. Martin Grisar, Wissembourg, both of France

[73] Assignee: Merrell Dow Pharmaceuticals Inc., Cincinnati, Ohio

[21] Appl. No.: 821,243

[22] Filed: Jan. 10, 1992

Related U.S. Application Data

[63] Continuation of Ser. No. 670,537, Mar. 15, 1991, abandoned.

[30] Foreign Application Priority Data

Mar. 16, 1990 [EP] European Pat. Off. ............ 90400731

[51] Int. Cl.⁵ .................... A61K 31/34; C07D 307/62
[52] U.S. Cl. ..................................... 514/471; 549/315
[58] Field of Search ......................... 514/471; 549/315

[56] References Cited

U.S. PATENT DOCUMENTS 4,368,330  1/1983  Andrews ............................. 549/315

FOREIGN PATENT DOCUMENTS 0277900  8/1982  European Pat. Off. .
0259707  3/1988  European Pat. Off. .
0202589  11/1988  European Pat. Off. .
2114571  8/1983  United Kingdom .

OTHER PUBLICATIONS

Chemiker-Zeitung 109(10) 341–343 (1985) by Franz Dallacker, et al., entitled "Derivate der L-Ascorbinsäure, Amino-6-desoxy-O²,O³-ethanidyl-und 6-Amino-6desoxy ascorbinsäuren".

Primary Examiner—C. Warren Ivy
Assistant Examiner—Amelia A. Owens
Attorney, Agent, or Firm—Carolyn D. Moon

[57] ABSTRACT

Derivatives of 3,4-dihydroxy-2,5-dihydrofuran-5-ones, intermediates and processes useful for their preparation are disclosed. These compounds are useful as free-radical scavengers and exhibit cellular protective properties.

16 Claims, No Drawings

ASCORBIC ACID DERIVATIVES

This is a continuation of application Ser. No. 07/670,537, filed Mar. 15, 1991 now abandoned.

FIELD OF THE INVENTION

This invention relates to derivatives of certain 3,4-dihydroxy-2,5-dihydrofuran-5-ones, to the intermediates and processes useful for their preparation, to their free-radical scavenger and cellular protective properties, and to their end-use application as therapeutic agents.

SUMMARY OF THE INVENTION

A compound of the formula

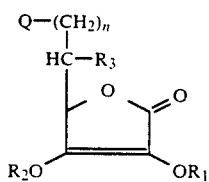

the enantiomers and mixtures thereof, the inner salts and the pharmaceutically acceptable salts thereof. Q is $NR_4R_5$ or $N^{\oplus}R_4R_5R_6 \cdot X^{\ominus}$, n is an integer 1 to 4. X is a halide or $OS(O)_2R_7$, with $R_7$ being $C_{1-6}$ alkyl, $(CH_2)_m$-Z substituted phenyl wherein m is 0,1,2,3 or 4 and Z is H, $C_{1-6}$ alkyl, $C_{1-6}$ alkoxy or halogeno, or nothing when $R_2$ is hydrogen. $R_1$ is H or $C_{1-20}$ alkyl. $R_2$ is H or $C_{1-20}$ alkyl or nothing when the inner salt is formed. $R_3$ is H, or OH, and each of $R_4$, $R_5$, and $R_6$ are $C_{1-6}$ alkyl, $(CH_2)_x$ aryl or $(CH_2)_x$ halogenated aryl, x being zero, or 1 to 6, with the proviso that when n is one and Q is $NR_4R_5$, then one of $R_1$ or $R_2$ is other than H.

The compounds of the present invention are used to treat tissues subject to reperfusion damage and to treat rheumatoid arthritis by administering a pharmaceutically effective amount of the compound to the subject in need of such therapy.

A process to prepare the compounds of the present invention is also disclosed.

DETAILED DESCRIPTION OF THE PRESENT INVENTION

This invention relates to derivatives of 3,4-dihydroxy-2,5-dihydrofuran-5-ones of the formula

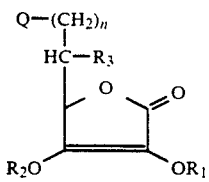

the enantiomers and mixtures thereof, the inner salts and the pharmaceutically acceptable salts thereof wherein Q is $NR_4R_5$ or $N^{\oplus}R_4R_5R_6 \cdot X^{\ominus}$, n is an integer 1 to 4, X is a halide or $OS(O)_2R_7$, with $R_7$ being $C_{1-6}$ alkyl, $(CH_2)_m$-Z substituted phenyl wherein m is 0,1,2,3 or 4 and Z is H, $C_{1-6}$alkyl, $C_{1-6}$ alkoxy or halogeno, or nothing when $R_2$ is hydrogen, $R_1$ is H or $C_{1-20}$ alkyl, $R_2$ is H, $C_{1-20}$ alkyl, or nothing when the inner salt is formed, $R_3$ is H, or OH, and each of $R_4$, $R_5$ and $R_6$ are $C_{1-6}$ alkyl, $(CH_2)_x$ aryl or $(CH_2)_x$ halogenated aryl, x being zero, or 1 to 6, with the proviso that when n is one and Q is $NR_4R_5$, then one of $R_1$ or $R_2$ is other than H.

As used herein, the $(CH_2)_n$ moiety of Formula I, wherein n is an integer 1 to 4, it is preferred that n be one or two. It is also contemplated that these carbon atoms may have one or both of their hydrogen atoms replaced with methyl groups. Preferably Q represents a quaternary moiety. In those instances wherein Q is $N^{\oplus}R_4R_5R_6 \cdot X^{\ominus}$, representing a quaternary ammonium derivative, it is preferred that all of the $R_4R_5R_6$ alkyl radicals be the same, preferably methyl or ethyl. However, within the contemplated scope of this invention are those moieties wherein one, two or all three are different. Another preferred group of quaternary compounds are those wherein $R_6$ represents $(CH_2)_x$ aryl, which includes phenyl, and preferably benzyl, phenethyl, phenypropyl, and phenylbutyl, which may be mono- or di-halogenated, preferably para chloro- or bromo-containing moieties. The preferred tertiary amines are those wherein $R_4$ and $R_5$ are methyl and/or ethyl and one of $R_1$ or $R_2$ is an alkyl radical. In those instances wherein X is a halogen, chloro and bromo are preferred. When X represents a sulfonate the preferred Z substituents are H, methyl, methoxy, chloro or bromo. The preferred ethers are those wherein $R_1$ contains an alkyl moiety designed to increase lipophilicity and includes those having straight or branched $C_{12}$ to $C_{20}$ carbon atoms, particularly octadecyl. Preferably $R_1$ is H or a long chain alkyl (e.g., $C_{14-20}$), preferably octadecyl.

In addition to the tertiary amines and quaternary ammonium moieties defined for Q of Formula I, cyclic heterocyclic moieties having one or two nitrogen atoms and which form 5 to 7 membered ring systems, including saturated and unsaturated manifestations are also contemplated as part of the definition of the Q moiety. Exemplary of such moieties are those derived from such compounds as pyrrolidine, piperidine, azepine, pyridine, pyrazine, piperazine, pyrrole, pyrroline and the like.

The term "pharmaceutically acceptable acid addition salts" embraces all those salts normally found useful in the pharmaceutical art, particularly those formed by the interaction of the base with such organic and inorganic acids as hydrochloric, hydrobromic, sulphuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono- or the di-acid salts can be formed, and such salts can exist in either a hydrated or a substantially anhydrous form. In those instances wherein $R_2$ is H, the compounds may form an inner salt, i.e., a zwitterion form, with the nitrogen atom of Q. Thus, in such instances the anion $X^{\ominus}$ may be deleted from the definition of Q. Such compounds are contemplated within the scope of this invention as defined in formula I. In general, salts of these compounds are crystalline materials which are soluble in water and various hydrophilic organic solvents.

In practice it is preferred to utilize those isomeric forms which most closely mimic the configuration of L-ascorbic acid (Ia). However, within the scope of this invention are included those isomeric forms analogous to D-isoascorbic acid (Ib), D-ascorbic acid and L-isoascorbic acid (Ic, Id, respectively). The generic structural formulae of the isomeric forms of this invention being

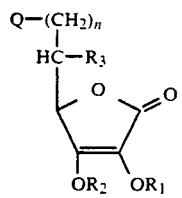
Ia

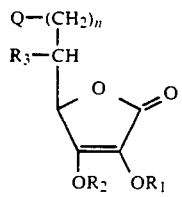
Ib

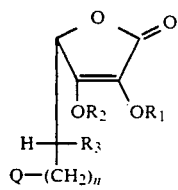
Ic

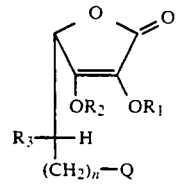
Id with $R_1$, $R_2$, $R_3$, n and Q being as previously defined. Preferred enantiomeric forms are those ($\beta$S,2R) enantiomers.

In general, the compounds of this invention may be prepared by methods analogously known in the art according to the following Reaction Scheme A.

Reaction Scheme A

Reaction Scheme A

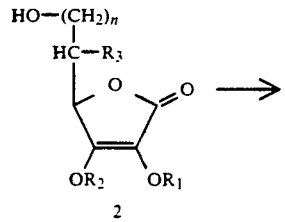
2

-continued
Reaction Scheme A

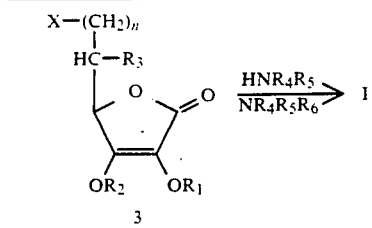
3 wherein $R_1$, $R_2$, $R_3$, X and n are as previously defined.

The first step of the reaction entails the activation of the alcohols (2) by their conversion to either their halides or tosylates, (i.e., X is iodo, chloro or preferably bromo or a sulfonyl radical of the formula $-OS(O)_2R_7$, $R_7$ being as previously defined). In the conversion of the alcohol to a halide, several routes are generally available, the choice being partially dependent upon whether the $R_1$ and $R_2$ are hydrogen or alkyl. These routes of conversion are: (a) treatment of the alcohol with a hydrohalide, (preferably HBr) in 33% acetic acid at about room temperature, (b) treatment of the alcohol with a tetrahalomethane, preferably $CBr_4$ with triphenylphosphine ($P\phi_3$) in such solvents as dimethylformamide, pyridine, acetonitrile and the like, under an inert atmosphere, (nitrogen or argon) and (c) treatment with hydrogen bromide informic acid according to the teachings of U.S. Pat. No. 3,043,937. Of course, in those instances wherein problems may arise by the presence of free hydroxyl groups, $R_1$ or $R_2$ are H and/or $R_3$ is OH, then such moieties may bear reaction-protecting groups such as benzyl, which may be readily removed by standard techniques following amination. Amination of the activated compounds of Formula 3 is effected by treatment of the halo or sulfonyl moiety-bearing compounds (as defined by X), with the appropriate amine in polar solvents, preferably methanol but also in ethanol, water, isopropanol or in acetonitrile, at from room temperature to about 60° C. In those instances wherein $R_2$ is H, then such compounds form an inner salt, such as depicted below.

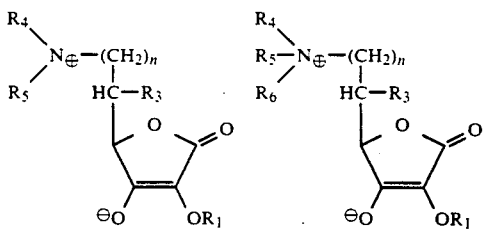
4  5

If desired, compounds 4 and 5 may be converted to their 3-O-alkyl derivatives by treatment with an alkyl halide.

Alternatively, compounds 3 may be reacted with a dialkyl amine ($R_4R_5NH_2$) and the tertiary amine may be treated with $R_6X$ to form the quaternary ammonium salts.

As stated, if desired, the hydroxyl groups of the intermediates may be selectively protected and deprotected by any appropriate method. One example of this protection and deprotection is illustrated in the following Reaction Scheme B.

Reaction Scheme B

Reaction Scheme B

[Chemical structures showing compounds 6, 7, and 8 with TrO—(CH₂)ₙ, OH, OPg, OR₁ groups and HO—(CH₂)ₙ derivative]

wherein Tr is a trityl protecting group, Pg is a reaction protecting group, preferably benzyl, and n and $R_1$ are as previously defined. The preparation of the compounds bearing the protecting, as well as the removal of these groups may be effected by standard procedures well known in the art.

The following examples illustrate preferred methods for the preparation of the compounds of Formula I.

EXAMPLE 1

2,5-Dihydro-β,3,4-trihydroxy-N,N,N-trimethyl-5-oxo-2-furanethanaminium, 3-hydroxide, inner salt A solution of 6-bromo-6-deoxy-L-ascorbic acid (8.33 g) and trimethylamine (20 ml) in methanol (70 ml) is stirred at room temperature under nitrogen for 4 days. The mixture is filtered and the residue is chromatographed on silica gel (isopropanol/water, 70:30). Recrystallization from methanol/water yields 3.26 g of the title compound as colorless crystals (m.p. 180° C. decomposed).

EXAMPLE 2

6-Deoxy-6-dimethylamino-L-ascorbic acid

Following the procedure described in Example 1, but using dimethylamine as the amine, the title compound is obtained (m.p. 230° C. decomposed).

EXAMPLE 3

2,5-Dihydro-β,3,4-trihydroxy-N,N-dimethyl-N-phenylmethyl-5-oxo-2-furanethanaminium, 3-hydroxide, inner salt Following the procedure described in Example 1, but using N,N-dimethyl-phenylmethylamine as the amine, the title compound is obtained (m.p. 225° C. decomposed).

EXAMPLE 4

2,5-Dihydro-β,3-dihydroxy-N,N,N trimethyl-4-octadecyloxy-5-oxo-2-furanethanaminium, 3-hydroxide, inner salt Step A 6-Bromo-6-deoxy-2-O-octadecyl-L-ascorbic acid To a stirred solution of 2-O-octadecyl-L-ascorbic acid (4.91 g) in dimethylformamide (100 ml) is added portionwise at 0° C. and under nitrogen carbon tetrabromide (3.65 g), followed by triphenylphosphine (2.88 g). The mixture is stirred overnight at room temperature and evaporated. The remaining residue is purified by column chromatography to give the 6-bromo derivative.

Step B

Following the procedure described in Example 1, but using the 6-bromo derivative prepared above, the title compound is obtained.

EXAMPLE 5

3-Butoxy-2,5-dihydro-β,4-dihydroxy-N,N,N-trimethyl-5-oxo-2-furanethanaminium, bromide Procedure I Step A 6-Bromo-6-deoxy-3-O-butyl-L-ascorbic acid Starting from 3-O-butyl-L-ascorbic acid and following the procedure described in Example 4, Step A, the title compound is obtained.

Step B

Using 6-bromo-6-deoxy-3-0-butyl-L-ascorbic acid and following the procedure described in Example 1 the 3-O-butyl-trimethylammonium derivative is obtained.

Procedure II

To a solution of 2,5-dihydro-β,3,4-trihydroxy-N,N,N-trimethyl-5-oxo-2-furanethanaminium (2.17 g) and 1-bromo-butane (1.37 g) in dimethylformamide (20 ml) is added potassium carbonate (1.38 g). The mixture is stirred overnight at room temperature and evaporated to dryness. The residue is then purified by column chromatography and recrystallized to give the title compound.

Having described the scope of the compounds of this invention as well as the generic and specific methods for preparing said compounds, the following information details the utility of the compounds of this invention.

When the blood supply to parts of the heart muscle is blocked, a myocardial infarct (heart attack) results and the deprived muscle tissue dies with the result of permanent heart damage. If the blood supply can be re-established within hours after infarction, the heart muscle tissue remains viable and permanent damage can be reduced. This can be accomplished by surgical as well as pharmacologic (thrombolysis) procedures and these processes are known as reperfusion.

Reperfusion is now widely and successfully applied and it has been claimed that fatalities due to myocardial infarction can be reduced by 20–30%. However, reperfusion also poses problems. Oxygen-deprived (ischemic) tissue finds itself in an abnormal state and is vulnerable when suddenly exposed to oxygen-rich blood. This has been termed the "oxygen paradox" and leads to reperfusion damage in the form of cell death. It has been postulated that this damage is due to oxygen-derived free radicals and, in particular, to the superoxide radical, $O_2^-$. Evidence for this hypothesis has been obtained in animal experiments. B. R. Lucchesi and coworkers showed that the enzyme superoxide dismutase, as well as the free radical scavenger N-(mercaptopropionyl)glycine reduce canine myocardial reperfusion injury (Cir. Res., 1984, 54, 277–285; J. Cardiovasc Pharmacol., 1986, 8, 978–88; Fed. Proc., 1987, 46, 2413–21).

The compounds of this invention possess a structure related to ascorbic acid, a natural substance known to possess anti-oxidant or free radical scavenger properties, and like ascorbic acid also are useful as pharmacologic antioxidants and free radical scavengers and, in particular, as scavengers of superoxide anion radical $O_2^-$. They can be therapeutically employed where reperfusion damage due to oxygen-derived free radicals and hydrogen peroxide causes cell death in tissues. This situation arises when total or partial blockade of blood supply to tissues is removed, either spontaneously (transient ischemia) or by pharmacologic or surgical intervention (thrombolysis, angioplasty, by-pass, organ transplant and the like). Tissues subjected to transient ischemia or reperfusion in various disease states, or by their medical treatment, are those of heart, lung, kidney, pancreas, intestine and brain. In particular, the now rapidly increasing practice of pharmacologic thrombolysis, also known as reperfusion, after coronary infarct and stroke, will benefit by prior or concomitant administration of a free radical scavenger such as the compounds of this invention. Similarly, surgical interventions, such as percutaneous transluminal coronary angioplasty, where a dilating balloon is used to increase the luminal diameter in severely occluded atherosclerotic vessels, coronary by-pass operations, and organ transplant surgery create conditions where reperfusion damage due to oxygen-derived radicals takes place and can be reduced by scavengers. Transient ischemia is one of the causative factors that lead to angina pectoris, and thus the compounds of this invention are also useful as anti-anginal agents. Additionally, particularly in the instance wherein Q represents a tertiary amine, the compounds are useful in the treatment of stroke.

The process of inflammation is also known to involve the release of superoxide radicals from phagocytic cells which cause some of the symptoms of rheumatoid arthritis and a free radical scavenger, such as the compounds of this invention, is also useful in the treatment of this disease as well as being useful in the treatment of inflammatory bowel disease. The compounds may also be useful in the treatment of cancers and of aging since oxygen-derived free radicals have been identified among causative factors. For reviews, see B. Halliwell and C. Gutteridge, Biochem. J., 1984, 219, 1–14; TINS 1985, 22–6.

A further utility of the compounds of this invention is for the treatment of cardiac arrhythmia, particularly that of the class III type and they also are useful in lowering blood-cholesterol levels, useful in treating cholesterol-induced atherogenosis.

In vitro and in vivo activity for the utility of the compounds of this invention may be demonstrated by the use of standard assays. Particularly useful for demonstrating the properties of the compounds of this invention are those assays which demonstrate the free radical scavenging property, affinity for cardiac tissue and cardioprotective properties. Based upon those assays, as well as by comparison with other compounds similarly useful for their anti-oxidant properties, the compounds of this invention will be effective when administered within the range from about 0.1 mg/kg to 50 mg/kg of body weight per day. For prophylactic administration, corresponding lower doses can be utilized.

Most preferably, the compounds are administered intravenously particularly under crisis situations wherein it is essential that the therapeutic agent be gotten to its site of action as quickly as possible, such as in those emergency conditions caused by coronary infarction, stroke and surgical interventions, conditions which can cause severe reperfusion damage. Otherwise, the compounds of this invention are administered intravenously wherein Q is a dialkylamino moiety, and orally in those instances wherein Q is a quaternary ammonium salt.

The compounds of this invention can be utilized both prophylactically and therapeutically in subjects. "Subjects" mean mammals, including humans. The amount of active ingredient for therapeutic administration can vary over a wide range and is dependent upon such factors as the age, health, sex and weight of the subject, as well as the nature and the severity of the condition being treated. Generally, a therapeutically effective amount of the active ingredient to be administered will range from about 0.1 mg/kg to 50 mg/kg of body weight per day. For prophylactic administration, corresponding lower doses can be utilized.

The compounds of this invention also can be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 100 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc, stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB.

Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added.

As is true in most instances wherein certain classes of compounds have been found to have beneficial therapeutic uses, certain members and sub-groups are preferred. In this instance those compounds wherein $R_4$ and $R_5$ are methyl or ethyl are preferred. Preferred $R_6$ moieties are methyl, ethyl, benzyl, phenethyl, phenyl propyl or phenylbutyl, particularly when the phenyl moiety bears one or two halo atoms, particularly chloro or bromo one of which being in the para position.

n is one or two, preferably one, $R_7$ is aryl or preferably aralkyl, most preferably benzyl, or a halogeno substituted benzyl, $R_1$ and $R_2$ preferably are hydrogen, but when they represent an alkoxy moiety, it is preferred that the alkyl moiety be the longer alkyl chains (particularly for $R_2$), straight or branched, within the limits of the definition for each alkyl group, particularly octadecyl, $R_3$ is preferably OH, OCH$_3$, or H, and X preferably is chloro or bromo or a sulfonate.

When $R_2$ is not H, halide salts are preferred.

In those instances wherein it is desired to protect cardiac tissue, it is preferred to utilize the quaternary ammonium compounds, said compounds preferably forming an inner salt when $R_2$ is H. Otherwise the tertiary amines are preferably utilized. The preferred enantiomers are the $\beta$S,2R isomers.

Particularly preferred compounds are those of the above examples and the $R_1$ octadecyl analogs thereof, the p-toluenesulfonate quaternary analogs thereof, the p-chlorophenylbutyl tertiary amines or quaternary analogs thereof, (i.e., one of $R_4$, $R_5$ or $R_6$ is a p-chlorophenylbutyl radical).

Particularly preferred compounds are those of the above examples and the $R_1$ octadecyl analogs thereof, the p-toluenesulfonate quaternary analogs thereof, the p-chlorophenylbutyl tertiary amines or quaternary analogs thereof, (i.e., one of $R_4$, $R_5$ or $R_6$ is a p-chlorophenylbutyl radical).

What is claimed is:

1. A compound of the formula

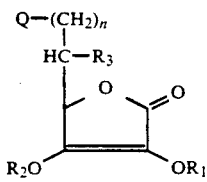

the enantiomers and mixtures thereof, the inner salts and the pharmaceutically acceptable salts thereof wherein Q is $NR_4R_5$ or $N^{\oplus}R_4R_5R_6 \cdot X^{\ominus}$, n is an integer 1 to 4, X is a halide or OS(O)$_2$R$_7$, with $R_7$ being $C_{1-6}$ alkyl, (CH$_2$)$_m$-Z substituted phenyl wherein m is 0,1,2,3 or 4 and Z is H, $C_{1-6}$ alkyl, $C_{1-6}$ alkoxy or halogen, or nothing when $R_2$ is nothing thereby forming the inner salt, $R_1$ is H or $C_{1-20}$ alkyl, $R_2$ is H, $C_{1-20}$ alkyl, or nothing when the inner salt is formed, $R_3$ is H, or OH, and each of $R_4$, $R_5$ and $R_6$ are $C_{1-6}$ alkyl, (CH$_2$)$_x$ aryl or (CH$_2$)$_x$ halogenated aryl, x being zero, or 1 to 6, with the proviso that when n is one and Q is $NR_4R_5$, then one of $R_1$ or $R_2$ is other than H.

2. The compound of claim 1 wherein the compound is in its $\beta$S,2R enantiomeric form.

3. The compound of claim 1 wherein Q is $N^{\oplus}R_4R_5R_6 \cdot X^{\ominus}$.

4. The compound of claim 1 wherein Q is $NR_4R_5$.

5. The compound of claim 3 wherein $R_4$, $R_5$ and $R_6$ are methyl or ethyl.

6. The compound of claim 5 wherein $R_2$ is H.

7. The compound of claim 6 wherein $R_1$ is octadecyl.

8. The compound of claim 4 wherein $R_4$ and $R_5$ are methyl.

9. The compound of claim 8 wherein $R_2$ is H.

10. The compound of claim 9 wherein $R_1$ is octadecyl.

11. The compound of claim 1 wherein $R_1$ and $R_2$ are H and $R_3$ is OH.

12. The compound of claim 1 wherein the compound forms an inner salt with R2 being nothing.

13. The compound of claim 1 wherein the compound is 2,5-dihydro-$\beta$,3,4-trihydroxy-N,N,N-trimethyl-5-oxo-2-furanethanaminium, 3-hydroxide, inner salt.

14. The compound of claim 1 wherein the compound is 6-deoxy-6-dimethylamino-L-ascorbic acid.

15. The compound of claim 1 wherein the compound is 2,5-dihydro-$\beta$,3,4-trihydroxy-N,N-dimethyl-N-phenylmethyl-5-oxo-2-furanethanaminium, 3 hydroxide, inner salt.

16. A process for treating tissues subject to reperfusion damage in a subject which comprises administering a pharmaceutically effective amount of a compound of the formula

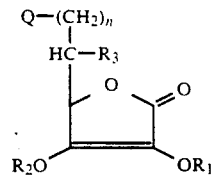

the enantiomers and mixtures thereof, the inner salts and the pharmaceutically acceptable salts thereof wherein Q is $NR_4R_5$ or $N^{\oplus}R_4R_5R_6 \cdot X^{\ominus}$, n is an integer 1 to 4, X is a halide or OS(O)$_2$R$_7$, with $R_7$ being $C_{1-6}$ alkyl, (CH$_2$)$_m$-Z substituted phenyl wherein m is 0,1,2,3 or 4 and Z is H, $C_{1-6}$ alkyl, $C_{1-6}$ alkoxy or halogen, or nothing when $R_2$ is hydrogen, $R_1$ is H or $C_{1-20}$ alkyl, $R_2$ is H, $C_{1-20}$ alkyl, or nothing when the inner salt is formed, $R_3$ is H, or OH, and each of $R_4$, $R_5$ and $R_6$ are $C_{1-6}$ alkyl, (CH$_2$)$_x$ aryl or (CH$_2$)$_x$ halogenated aryl, x being zero, or 1 to 6, with the proviso that when n is one and Q is $NR_4R_5$, then one of $R_1$ or $R_2$ is other than H.

* * * * *